(12) United States Patent
Peña Cabrera et al.

(10) Patent No.: US 8,664,385 B2
(45) Date of Patent: Mar. 4, 2014

(54) SYNTHESIS OF BORON DIPYRROMETHENES WITH LASER PROPERTIES

(75) Inventors: Eduardo Peña Cabrera, Guanajuato (MX); Ismael Javier Arroyo Cordova, Guanajuato (MX); Fabiola Irene Lopez Vallejo, Guanajuato (MX)

(73) Assignee: Universidad de Guanajuato, Guanajuato (MX)

( * ) Notice: Subject to any disclaimer, the term of this patent is extended or adjusted under 35 U.S.C. 154(b) by 0 days.

(21) Appl. No.: 13/498,969

(22) PCT Filed: Sep. 30, 2010

(86) PCT No.: PCT/MX2010/000100
§ 371 (c)(1),
(2), (4) Date: Jun. 4, 2012

(87) PCT Pub. No.: WO2011/040800
PCT Pub. Date: Apr. 7, 2011

(65) Prior Publication Data
US 2012/0245362 A1    Sep. 27, 2012

(30) Foreign Application Priority Data
Sep. 30, 2009   (MX) .................... MX/a/2009/010555

(51) Int. Cl.
*C07F 5/02* (2006.01)
(52) U.S. Cl.
USPC ........................................................ 544/229
(58) Field of Classification Search
USPC ........................................................ 544/229
See application file for complete search history.

(56) References Cited
U.S. PATENT DOCUMENTS
2010/0286510 A1   11/2010   Pinchuk et al.

*Primary Examiner* — Shawquia Young
(74) *Attorney, Agent, or Firm* — Panitch Schwarze Belisario & Nadel LLP

(57) ABSTRACT

A family of three 8-alkyl boron dipyrromethenes 1, 2, and 3 has been prepared. These compounds are characterized by emission in the green region of the electromagnetic radiation spectrum and exhibit an almost double laser efficiency than other commercial dyes and much greater photostability. The 8-alkyl boron dipyrromethenes are prepared by catalytic hydrogenation (reduction) of the corresponding 8-alkenyl boron dipyrromethenes, which are obtained by Liebeskind-Srogl coupling of thiomethylboron dipyrromethene with an alkenyl boronic acid.

1

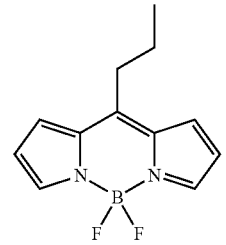

2

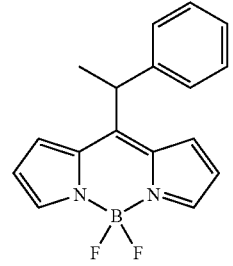

3

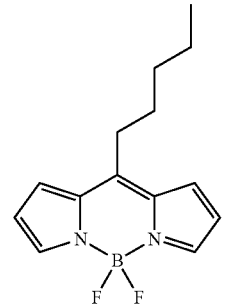

4 Claims, No Drawings

SYNTHESIS OF BORON DIPYRROMETHENES WITH LASER PROPERTIES

CROSS-REFERENCE TO RELATED APPLICATIONS

This application is a Section 371 of International Application No. PCT/MX2010/000100, filed Sep. 30, 2010, which was published in the Spanish language on Apr. 7, 2011, under International Publication No. WO 2011/040800 A2 and the disclosure of which is incorporated herein by reference.

BACKGROUND OF THE INVENTION

Since their discovery in 1968, boron dipyrromethenes have been synthesized by complex methodologies which involve several steps, long reaction times, tedious purification, and low yields. Since 1990, the possible application of boron dipyrromethenes as lasers has been described in the literature. However, these kinds of compounds are not available on the market, and those that are accessible, such as coumarins, are very expensive.

BRIEF SUMMARY OF THE INVENTION

The invention is directed to the synthesis of three different 8-alkyl boron dipyrromethenes from 8-alkenyl boron dipyrromethene precursors. These 8-alkyl boron dipyrromethenes have great potential for application as laser dyes because they emit within the green spectrum range, have a greater efficiency of up to 1.8 times higher than other commercial dyes used to manufacture lasers, and also exhibit an intensely higher photostability than such commercially available materials. The method involves first synthesizing 8-alkenyl boron dipyrromethenes, which are precursors for 8-alkyl boron dipyrromethenes. Catalytic reduction of the 8-alkenyl boron dipyrromethenes by hydrogenation yields compounds having formulas 1, 2, 3.

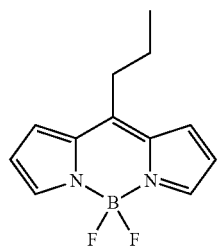

1

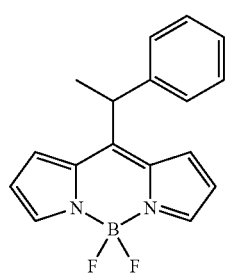

2

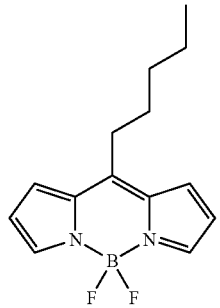

3

These compounds have the advantages of higher laser yield than commercial coumarins 540A and 503 used for the same purpose. Additionally, their synthesis takes place in only two steps. Another advantage of this type of compounds is their structure, which is relatively simple and has no bulky functional groups, which results in ease of synthesis.

More specifically, the invention relates to a family of 8-alkyl boron dipyrromethenes (three compounds) which are synthesized from the corresponding 9-alkenyl boron dipyrromethene precursors. The precursors are obtained via a Liebeskind-Srogl coupling using a catalytic quantity of palladium(0), 7.5% trifuryl phosphine (TFF) and a stoichiometric quantity (3 equivalents) of a Cu(I) salt, as shown in Equation 1.

Equation 1

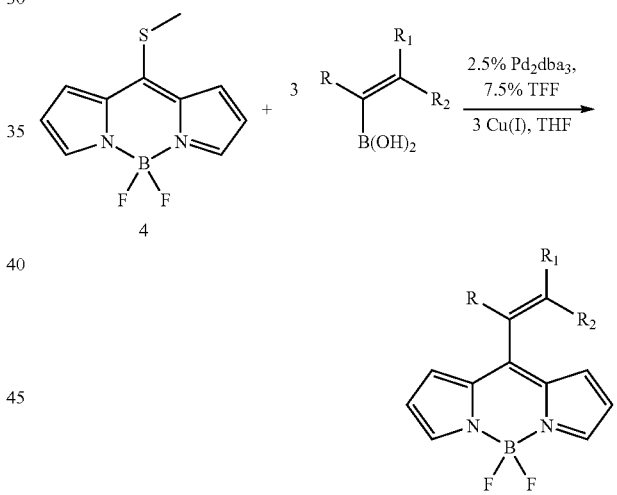

Subsequently, catalytic reduction is performed with hydrogen using palladium on carbon as a catalyst (Equation 2) to yield the 8-alkyl boron dipyrromethenes.

Equation 2

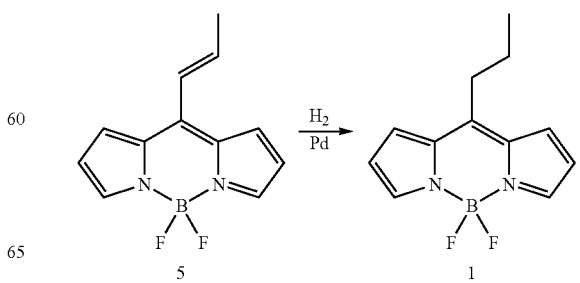

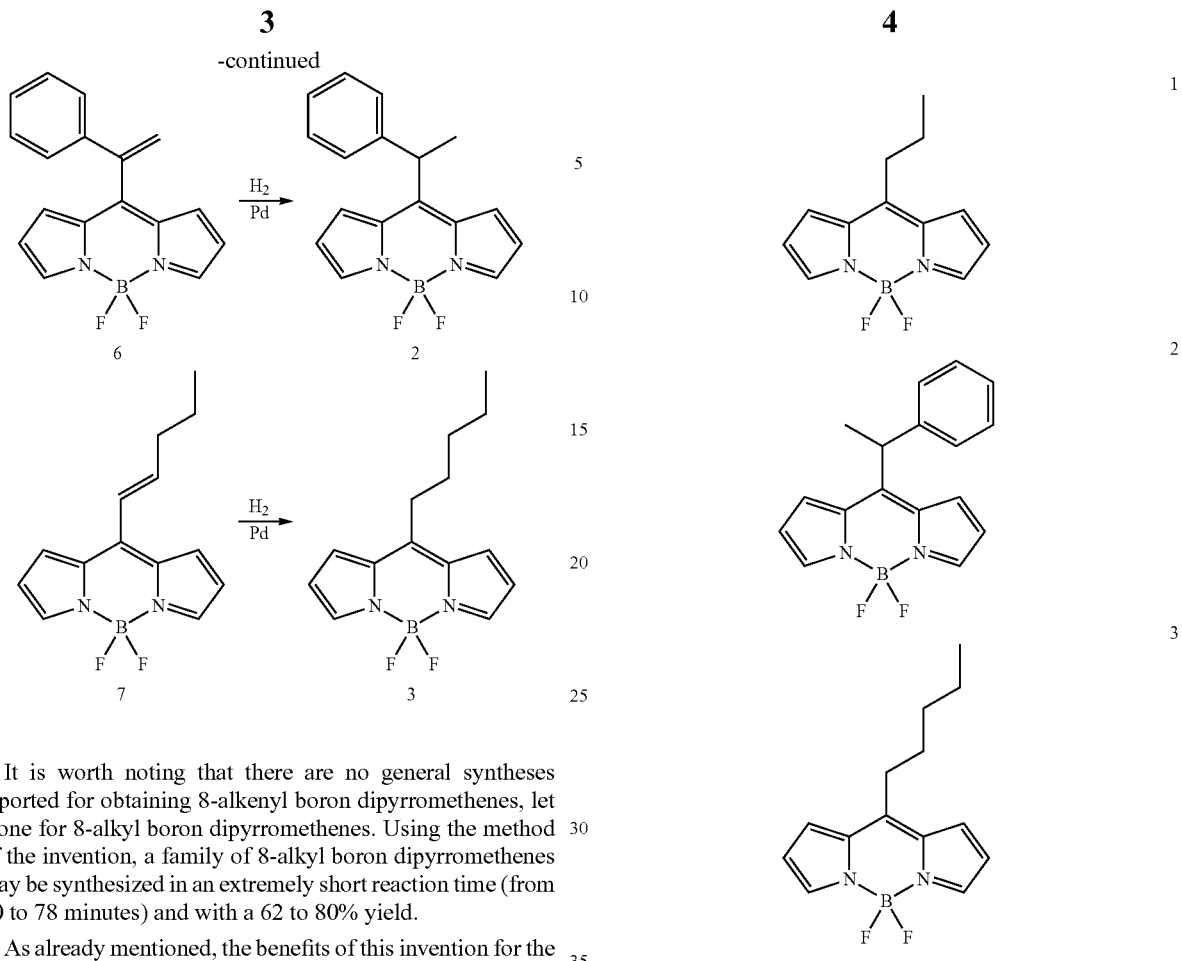

It is worth noting that there are no general syntheses reported for obtaining 8-alkenyl boron dipyrromethenes, let alone for 8-alkyl boron dipyrromethenes. Using the method of the invention, a family of 8-alkyl boron dipyrromethenes may be synthesized in an extremely short reaction time (from 20 to 78 minutes) and with a 62 to 80% yield.

As already mentioned, the benefits of this invention for the synthesis of 8-alkenyl boron dipyrromethenes are the reaction times and the Liebeskind-Srogl coupling using mild conditions to synthesize them. This coupling uses neutral reaction conditions. Another important advantage is the use of alkenyl boronic acids in the process, which are commercially available. The catalytic hydrogenation is performed with mild conditions as well, using ethanol, molecular hydrogen, palladium on carbon, and stirring.

Therefore, the novelty of this invention is the 8-alkyl boron dipyrromethene synthesis process, and the application of these compounds as laser dyes. At present there are molecules, such as coumarins and other more complex boron dipyrromethenes, for use as laser dyes, but their preparation is very expensive due to their complex synthesis route. However, the synthesis developed, as discussed, is relatively simple, swift, and allows for a family with laser emission in the green spectrum range.

Our research group develops dyes with very interesting optical properties. In preparing the three members of the family of 8-alkyl boron dipyrromethenes, laser efficiency was determined. The results obtained demonstrated that the compounds can be used as laser dyes with greater efficiency than commercial compounds, and have a wavelength emission with very interesting applications.

DETAILED DESCRIPTION OF THE INVENTION

The invention is directed to a family of three 8-alkyl dipyrromethenes having formulas 1, 2, 3: 8-propyl-boron dipyrromethene (1), 8-(1-phenylethyl)boron dipyrromethene (2), and 8-pentyl boron dipyrromethene (3).

These compounds are prepared in a two step synthesis. First, the corresponding alkenyl boron dipyrromethene is synthesized via a cross Liebeskind-Srogl coupling that is performed selectively on the 8 position of thiomethyl boron dipyrromethene. Alkenyl boronic acids are used to functionalize that position and obtain the desired products; there are no reports regarding any alternative syntheses. Such compounds are obtained in yields ranging from 79 to 97%, within a time period of not longer than 30 minutes, and are considered to be good.

As shown in Equation 1, in this coupling, 1.0 equivalent of thiomethylboron dipyrromethene 4 is reacted with 3.0 equivalents of alkenyl boronic acid, using a catalytic system made of 2.5% trisdibenzylideneacetone Pd 0 ($Pd_2dba_3$), 7.5% trifuryl phosphine (TFF) and 3.0 equivalents copper thiophencarboxylate (CuTC) to yield the 8-alkenyl boron dipyrromethenes 5, 6, 7, which are precursors of 1, 2 and 3.

Equation 1

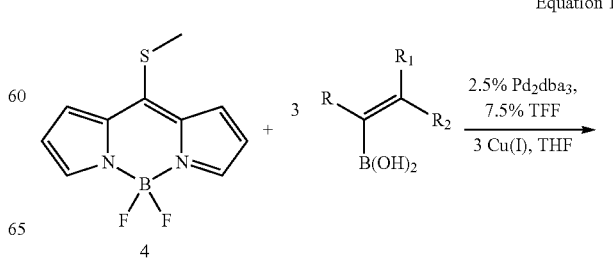

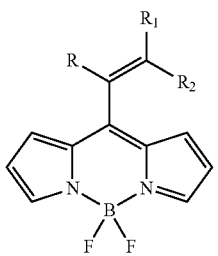

The next step (Equation 2) involves catalytic hydrogenation (reduction) in an ethanolic medium with molecular hydrogen, using palladium on carbon as a catalytic system. In this step, molecules of the 8-alkyl boron dipyrromethenes family are obtained in yields ranging from 62 to 80%, within time periods not longer than 78 minutes.

Equation 2

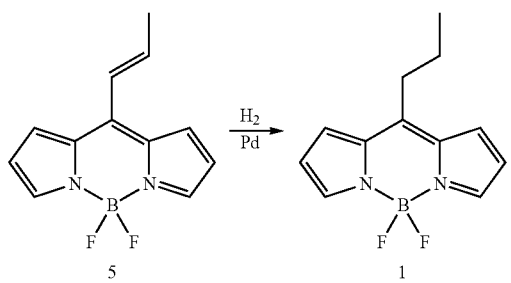

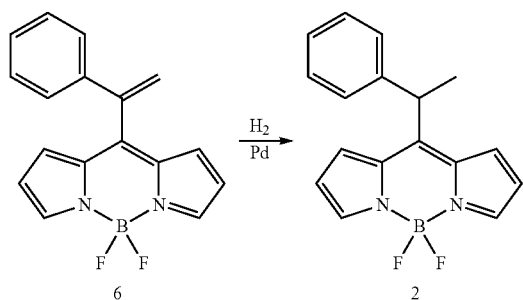

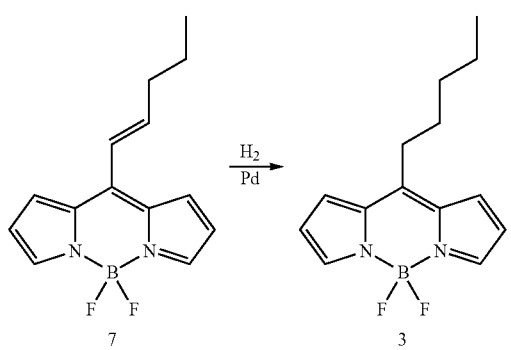

The invention will not be described in conjunction with the following, non-limiting examples.

EXAMPLES

Synthesis

Compounds 1, 2, and 3, were synthesized via precursors 5, 6, and 7, and have the following characteristics:

8-propylboron dipyrromethene (1)

The synthesis was performed using a reaction time of 20 minutes and had a yield of 97% in the first step; in the second step, after 55 minutes, the yield was 88% yield. The product appeared as orange crystals. CCF (20% AcOEt/Hexanes) $R_f$=0.4 cm; p.f. 65.0-66.0° C.; IR (KBr, cm$^{-1}$): 955(f), 1072 (f), 1115(f), 1262(f), 1396(f), 1414(f), 1571(f), 706(m), 739 (m), 779(m), 2875(m), 2927(m), 2962(m), 588(d), 621(d), 2336(d), 3111(d); $^1$H RMN (200 MHz, CDCl$_3$) δ: 1.06 (6H, m, J=7.4 Hz), 1.85 (2H, m, J=7.4 Hz), 2.92 (2H, m, J=7.6 Hz), 6.54 (2H, d, J=3.6), 7.30 (2H, s), 7.86 (2H, s); 13C RMN (75.5 MHz, CDCl$_3$), δ: 14.7, 27.3, 33.2, 118.1, 128.1, 135.5, 143.6, 151.1.

This compound has a laser efficiency of 23.6% in ethyl acetate using a 355 nm Nd YAG laser as an excitation wavelength.

8-phenylethylboron dipyrromethene (2)

The synthesis was performed using a reaction time of 30 minutes and had a yield of 88% in the first step; in the second step, after 78 minutes, the yield was 62% yield. The product appeared as green crystals, CCF (20% AcOEt/Hexanes) $R_f$=0.7 cm; p.f. 70.0-72.0° C.; IR (KBr, cm$^{-1}$): 1055(f), 1070 (f), 1083(f), 1095(f), 1253(f), 1394(f), 1556(f), 701(m), 734 (m), 771(m), 941(m), 983(m), 1231(m), 1354(m), 586(d), 2922(d), 3112(d), 3693(d); $^1$H RMN (200 MHz, CDCl$_3$) δ: 1.26 (2H, s), 1.93 (3H, d, J=7.4 Hz), 4.75 (1H, m, J=7.2 Hx), 6.46 (2H, d, J=3.0 Hz), 7.13 (2H, d, J=4.4 Hz), 7.31 (3H, m), 7.36 (4H, d, J=4.6 Hz), 7.84 (2H, s); 13C RMN (75.5 MHz, CDCl$_3$), δ: 22.1, 29.9, 40.8, 118.4, 127.3, 129.0, 129.5, 135.0, 143.0, 143.7, 155.0.

This compound has a laser efficiency of 0.84% in ethyl acetate using a 355 nm Nd YAG laser an excitation wavelength.

8-pentyl boron dipyrromethene (3)

The synthesis was performed using a reaction time of 12 minutes and had a yield of 79% in the first step; in the second step, after 20 minutes, the yield was 75%. The product appeared as orange crystals. CCF (20% AcOEt/Hexanes) $R_f$=0.8 cm; p.f. 51.5-52.0° C.; IR (KBr, cm$^{-1}$): 704(f), 732(f), 767(f), 952(f), 1062(f), 1112(f), 1257(f), 1392(f), 1565(f), 865(m), 1195(m), 1228(m), 1355(m), 1463(m), 1482(m), 2929(m), 1303(d), 2861(d), 2956(d), 3120(d); $^1$H RMN (200 MHz, CDCl$_3$) δ: 0.92 (3H, dd, J=6.2, 7.0 Hz), 1.43 (4H, dd, J=3.6, 13.3 Hz), 1.80 (2H, m, J=7.0 Hz), 2.93 (2H, m, J=7.8 Hz), 6.54 (2H, d, J=3.4 Hz), 7.28 (2H, d, J=5.8 Hz); 13C RMN (75.5 MHz, CDCl$_3$), δ: 14.1, 22.5, 31.4, 32.3, 33.8, 118.1, 128.0, 135.4, 143.4, 151.5.

This compound has a laser efficiency of 19.7% in ethyl acetate using a 355 nm.Nd YAG laser as an excitation wavelength.

The compounds according to the invention have the major advantage of exhibiting 240 times greater laser efficiency than other molecules, such as coumarins. Another advantage, as already mentioned, is that the synthesis is simple because it requires 5 hours or less to obtain pure products, and all of the reagents are commercially available. These compounds emit within the green region of the electromagnetic radiation spectrum, and lasers emitting within the green region, due to their power, have significant applications in medicine and biotechnology.

Laser Efficiency Analysis

First, laser efficiency was evaluated in liquid phase epitaxy as a function of concentration and solvent, allowing determination of the ideal working concentration and giving an idea of the monomers to be used in the further solid phase study. The optimum concentration for maximum laser efficiency was determined to be 3.0 mM. At lower concentrations, the excitation light passes through the sample so that its emission is not confined to the surface of the cuvette. It was observed that, in general, the synthesis dye had greater laser efficiency than other solvents studied, such as acetone, methanol, ethanol, and trifluoroethanol (except in cyclohexane). Due to the higher efficiency levels shown in acetone and trifluoroethanol, methyl methacrylate (MMA) and trifluoroethyl methacrylate (TFMA) were chosen as monomers for the solid matrix synthesis.

The laser efficiency of 8-propylboron dipyrromethene (1) was then evaluated in an aqueous phase using methacrylic matrixes. This dye was incorporated in different methacrylic matrixes and its efficiency and laser stability were determined when irradiated with a 355 nm Nd:YAG laser at a repetition frequency of 5 Hz and an energy of 5.0 mJ/pulse.

To select a matrix it is necessary to reach a compromise between efficiency and stability, and in this case, a PMMA matrix had proven better results. The following results were obtained in this study:

| | Laser efficiency/stability in lineal matrixes for 8-propylboron dipyrromethene | | | | |
|---|---|---|---|---|---|
| PMMA | Max. laser efficiency (%) | λ Max emission. (nm) | Δλ (nm) | No. of pulses (stability 50%) | Final stability % |
| 10 | 24.5 | 537.1 | 2.51 | 17143 | $43.3_{17300p}$ |

| | Laser efficiency/stability for 8-propylboron dipyrromethene in fluoridated matrixes | | | | |
|---|---|---|---|---|---|
| COP (MMA/ TFMA) | Max. laser efficiency (%) | λ Max emission (nm) | Δλ (nm) | No. of pulses (stability 50%) | Final stability % |
| 9/1 | 27.1 | 536.4 | 2.76 | — | $53.6_{11000p}$ |
| 7/3 | 18.5 | 535.5 | 3.52 | — | $58.7_{5500p}$ |

At the same time, a comparative test with the Coumarin 540A commercial dye was performed, which emits within the same spectral region. Coumarin 540A was also introduced in PMMA but it did not show any laser emission under these matrix synthesis conditions, and therefore it is not possible to compare both results directly. However, prior results from another similar coumarin, CU 503 (*Appl. Phys. B,* 67 (1998) 167-173), provide the following comparative data: Coumarin 503: 5.10-3 M, laser N2, pumping energy 1.2 mJ/pulse, repetition frequency 2 Hz.

| Coumarin Laser efficiency | | | | |
|---|---|---|---|---|
| PMMA | Max. Laser efficiency (%) | λ Max emission (nm) | Δλ (nm) | Final stability % |
| 10 | 15 | 473 | 9 | $0_{1700p}$ |

To summarize, these results demonstrate that there is a new boron dipyrromethene laser that emits light within the green region of the spectrum (wavelengths of interest for various applications), with considerable laser efficiency, and photostability significantly higher than commercial coumarins currently used as laser dyes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing an 8-alkyl boron dipyrromethene, comprising performing a Liebeskind-Srogl coupling in the 8 position of a thiomethylboron dipyrromethene with an alkenyl boronic acid to produce an 8-alkenyl boron dipyrromethene, and reducing the 8-alkenyl boron dipyrromethene to yield the 8-alkyl boron dipyrromethene.

2. The method according to claim 1, wherein the reduction is performed with molecular hydrogen using palladium on carbon as a catalyst.

3. The method according to claim 1, wherein the 8-alkyl boron dipyrromethene has formula 1, 2, or 3:

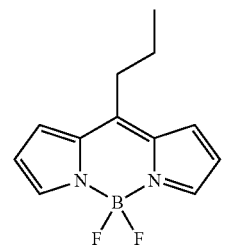

1

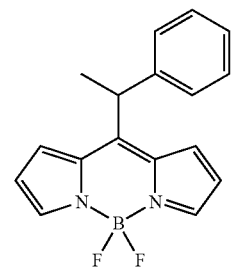

2

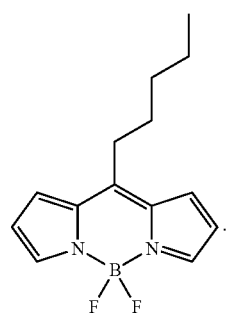
4. The method according to claim 1, wherein the 8-alkyl boron dipyrromethene exhibits a high laser efficiency with emission in the green region of an electromagnetic radiation spectrum.
* * * * *